United States Patent [19]

Bonte et al.

[11] Patent Number: 4,765,987
[45] Date of Patent: Aug. 23, 1988

[54] ARTIFICIAL SURFACTANTS, PHARMACEUTICAL COMPOSITIONS CONTAINING THEM AND USE THEREOF

[75] Inventors: Frédéric Bonte, Boulogne; Michel Dehan, Verrieres le Buisson; Alain Le Ridant, Neuilly sur Seine; Francis Puisieux, Maisons Alfort; Christiane C. Taupin, Orsay, all of France

[73] Assignee: ADIR & Cie, Neuilly-sur-Seine, France

[21] Appl. No.: 899,656

[22] Filed: Aug. 25, 1986

[30] Foreign Application Priority Data

Aug. 30, 1985 [FR] France .................. 85 12950

[51] Int. Cl.$^4$ ............... A61K 37/22; A61K 9/42; B01J 13/02; C07F 9/10
[52] U.S. Cl. ..................... 424/450; 252/356; 264/4.6; 428/402.2; 436/829; 514/78
[58] Field of Search ............ 252/356; 264/4.6; 428/402.2; 424/450; 514/78; 436/829

[56] References Cited

U.S. PATENT DOCUMENTS

| | | | |
|---|---|---|---|
| 4,310,506 | 1/1982 | Baldeschwieler et al. | 424/450 X |
| 4,312,860 | 1/1982 | Clements | 514/78 |
| 4,394,372 | 7/1983 | Taylor | 514/786 X |
| 4,515,736 | 5/1985 | Deamer | 424/450 X |
| 4,673,567 | 6/1987 | Jizomoto | 264/4.6 X |

FOREIGN PATENT DOCUMENTS 81108298.1 10/1979 European Pat. Off. .
83304596.6 8/1983 European Pat. Off. .
2900300 1/1979 Fed. Rep. of Germany .

Primary Examiner—Richard D. Lovering
Attorney, Agent, or Firm—Gordon W. Hueschen

[57] ABSTRACT

New artificial surfactants composed of dipalmitoylphosphatidylcholine, distearoylphosphatidylcholine and soya lecithin and pharmaceutical compositions containing them, which can be used to replace deficient endogenous pulmonary surfactant.

12 Claims, 1 Drawing Sheet

Surface pressure-area isotherms obtained by the surfactant of Example 1

Surface pressure-area isotherms obtained by the surfactant of Example 1

Surface pressure-area isotherms obtained by the surfactant of Example 2

ARTIFICIAL SURFACTANTS, PHARMACEUTICAL COMPOSITIONS CONTAINING THEM AND USE THEREOF

The present invention relates to new artificial pulmonary surfactants, to a process of the preparation thereof, and to pharmaceutical compositions containing them.

IN THE DRAWINGS

In the drawings,
FIG. 1 and FIG. 2 represent the isotherms of Examples 1 and 2 at 37° C., as will be further discussed hereinafter under the heading of "STUDY OF SURFACE PROPERTIES".

BACKGROUND OF THE INVENTION

Pulmonary surfactant is the name given to all the surface-active substances that reduce the surface tension of the alveolar gas-liquid boundary layer. Pulmonary surfactant, which extends as a very fine film (monolayer) on the surface of the millions of small pulmonary alveoli, plays a very important physiological role. It permits the intra-alveolar surface tension to fall during expiration, thus allowing a residual volume of gas to be maintained, which is necessary for the continuous exchange of oxygen and carbon dioxide between the pulmonary capillary and the alveolar gas. A deficiency of endogenous surfactant causes disturbances of respiratory function.

It is known that these disturbances in children born prematurely are responsible for the disease of the hyaline membranes. Moreover, considerable deficiencies of endogenous surfactant are also encountered in adults having pulmonary infections, in people poisoned by gases and in certain people who have suffered severe burns.

For the treatment of deficiencies of endogenous surfactant and with the aim of replacing the deficient pulmonary surfactant, there have recently been employed exogenous surfactants of natural origin or artificial compositions containing surface-active materials. Exogenous surfactants are characterised by a certain number of physicochemical properties which are essential to their use in achieving the desired aim. They must be active at 37° C. and be able to spread out on the alveolar interface in the form of a monomolecular film. This monolayer of surfactant which is compressed at the air-water interface must permit a low surface tension (from 0 to 9 $mN.m^{-1}$) to be obtained in order to avoid alveolar collapse, and this must be possible for a sufficient length of time during respiratory cycles. Furthermore, exogenous surfactants must maintain continuous gaseous alveolo-capillary exchange, be non-toxic and well tolerated when used therapeutically.

Pulmonary surface-active products extracted from the lungs of mammals have the properties indicated above, but they inevitably contain a considerable amount of so-called foreign proteins and are generally contaminated by many microorganisms. These products can therefore be used only after an often vary lengthy and costly purification process.

Several processes are known at present (French Pat. No. 80.11680, Japanese Application No. 58 164 513, Japanese Application No. 58,183,620, European Application No. 119 056, Japanese Application No. 58 045 299), but their use is of little value because the raw materials of animal origin are difficult to obtain and are non-uniform.

Experience has shown that it is possible to use artificial surfactants in therapeutics provided that they have a certain number of physical characteristics and that their chemical composition is similar to that of the natural surfactant.

The biochemical composition of human surfactant is not known with certainty because of its complexity and the diversity of the methods used, but it is generally accepted that it is composed of 85% phospholipids, 13% proteins and 2% miscellaneous substances. The lipid fraction, which is responsible for almost all the surface-active power of the surfactant, is composed principally of saturated phospholipids. The major component is dipalmitoylphosphatidylcholine, which is known to reduce the alveolar surface tension to below 1 $mN.m^{-1}$ under dynamic pressure. Several artificial mixtures that contain carbohydrates, amino acids, fatty acids or alcohols having a high molecular weight and that have dipalmitoylphosphatidylcholine as the principal constituent are already known (Japanese Applications Nos. 58 183 621 and 58 135 813, American Patent No. 4 312 860, German Application No. 29 00 300), but the artificial mixtures are especially binary mixtures of phospholipids that also contain phosphatidylglycerol which have been described and used preferentially in therapeutics (C. J. Morley et al. The Lancet, 1981, 1 64–68, German Application No. 32 29 179, European Application No. 110 498). Phosphatidylglycerol has, in fact, for a long time been considered one of the indispensable constituents of an artificial surfactant.

Hitherto, tests in vitro have shown that no artificial surfactant containing dipalmitoylphosphatidylcholine and phosphatidylglycerol has surface properties that are identical with those defined by study of the natural surfactant. These results led to the expectation that their activity in vivo would be average, which, moreover, was confirmed after they had been tested clinically. On the other hand, the use of phosphatidylglycerol for the preparation of artificial surfactants presents several disadvantages. It is costly and difficult to supply, because its instability involves storing it in an organic solvent at a temperature much lower than room temperature. Moreover, because it is obtained enzymatically from egg lecithin, batches thereof have very variable physicochemical characteristics.

The Applicant has now discovered a group of novel artificial surfactants which are easily made use of with industrially obtainable raw materials and which have all the physical characteristics of natural human surfactant.

The invention relates more precisely to artificial surfactants, characterised in that they contain ternary mixtures of dipalmitoylphosphatidylcholine, distearoylphosphatidylcholine and soya lecithin and in that they are composed of:

(1) from 10 to 70 mol % of dipalmitoylphosphatidylcholine,
(2) from 10 to 70 mol % of distearoylphosphatidylcholine,
(3) from 10 to 30 mol % of soya lecithin, wherein the sum of the constituents indicated under 1 to 3 must, in each case, be equal to 100 mol %.

In view of their use for compensating for a deficiency of endogenous pulmonary surface-active material, the artificial surfactants of the invention are presented in various sterile pharmaceutical forms which are suitable for direct administration in the trachea.

The liposome form may be mentioned by way of a non-limiting example. The concentration of one of the artificial surfactants forming the subject of the present invention in the liposomes may vary between 1 mg.ml$^{-1}$ and 100 mg.ml$^{-1}$.

The invention also includes pharmaceutical compositions containing as carrier the artificial surfactants described above in a suitable form and containing one or more other compounds which may be used therapeutically in the treatment of disorders caused by a deficiency of endogenous pulmonary surfactant, such as enzymes, vitamins, etc.

The constituents of the artificial surfactants of the invention are known substances which are available commercially. Their preparation is described in the literature.

Dipalmitoylphosphatidylcholine is marketed among others by SIGMA CHEMICAL COMPANY St. LOUIS, Mo, U.S.A. (99% purity). It has a molecular weight of 734 and the chemical formula:

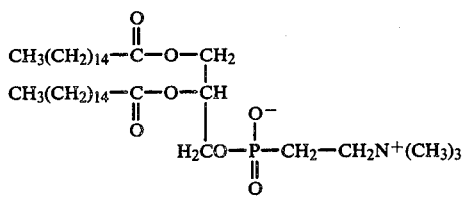

Distearoylphosphatidylcholine is also a compound which is at present marketed by SIGMA CHEMICAL COMPANY St. LOUIS, Mo, U.S.A. (99% purity). Its molecular weight is 790 and it has the following chemical formula:

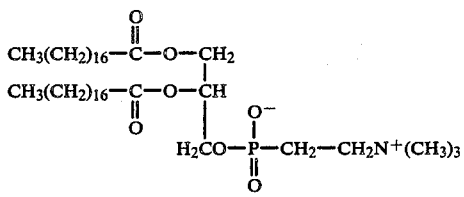

Soya lecithin is a raw material which has been used for a long time in human medicine, especially for the preparation of galenic forms administered intravenously. It is marketed in particular under the mark "Epikuron 200"® by LUCAS MEYER (Hamburg, Federal Republic of Germany). Its exact composition is known (Bergenstahl B. et al., Progr. Colloid. & Polymer. Sci. (1983), 68, 48–52). Its molecular weight is 780. Soya lecithin is easily obtained, is of low cost, and batches thereof are of a constant quality and composition.

Liposomes containing one of the artificial surfactants of the invention may be prepared according to the process described by Bangham (Bangham A. D. Ann. Rev. Biochem., 1972, 41, 735–776). The constituents of the surfactant are dissolved in a suitable solvent, such as chloroform. The resulting solution is subjected to rotary evaporation under reduced pressure at a temperature of from 30° to 50° C. until the solvent has been completely removed and a fine film of lipid has formed. The last traces of solvent are carried away by a stream of nitrogen and the film is then taken up in an amount of water or in a physiologically tolerable aqueous solution, and is subjected to a continuous rotary movement. The lipids thus dispersed in the aqueous phase form liposomes spontaneously.

In order to obtain sterile liposomes of a well defined size, certain precautions and additional steps are necessary; the liposomes are prepared under aseptic conditions and, after they have formed, are subjected to the action of ultrasound and to sterile filtration.

The artificial surfactants according to the invention have very valuable physicochemical properties and, more particularly, surface-active properties and are distinguished from the other artificial surfactants already known.

Tests in vitro have shown that they meet all the criteria of quality of an exogenous pulmonary surfactant and that they have surface properties which are identical with those of natural surfactants. Moreover, tests in vivo have shown that they are well tolerated by animals.

The endogenous surfactant is regarded as a monomolecular phospholipid layer at the alveolar interface. The description of the characteristic properties of such a surface-active layer in vitro is effected by means of a pressure-area curve which shows the relationship between the observed surface pressure and the area occupied by the molecules of the film on the liquid surface. The surface pressure II, which is defined as the reduction in interfacial tension caused by the monolayer, is equal to the difference between the surface tension of the pure liquid and the surface tension of the liquid when covered by the surface-active film. This reduction in surface tension is the principal criterion of the activity of a surfactant. The surface pressure-area isotherms are produced on a film balance, under conditions close to physiological reality, during compression-expansion cycles which simulate expiration-inspiration respiratory cycles. At the end of compression, a good exogenous surfactant should have a surface pressure of approximately 72 mN.m$^{-1}$, which corresponds to a surface tension of approximately zero.

A study of the surface pressure-area isotherms of the pulmonary surfactant of rabbits (Beppu O. et al., J. Appl. Physiol.: Respirat. Environ. Exercise Physiol. 1983, 55(2) 496–502) and of a natural surfactant isolated from human amniotic fluid (Hallman M. et al., Pediatrics, 1983, 71, No. 4, 473–482) recently revealed, apart from the plateau of the final collapse, the existense of an intermediate plateau. As a result of these two plateaux and therefore of the coexistence of two phases, one solid and one liquid, of the constituents of the surfactant, there are obtained both a high surface pressure at the end of compression, which is necessary to avoid alveolar collapse, and a not inconsiderable pressure on large areas which contributes to the reduction in the ventilatory effort. This coexistence of the phases is also involved in improving the manner in which the surfactant spreads out again, which is necessary for a long activity of surface-active substances.

The surface pressure-area isotherms of the artificial surfactant compositions of the invention also have this intermediate plateau. These compositions therefore have the characteristics of the natural surfactants indicated above. Moreover, tests in vitro have shown that the compositions of the invention are adsorbed spontaneously at the interface and produce a maximum pressure at the end of compression of approximately 72 mN.m$^{-1}$. As indicated above, this pressure corresponds to the pressure necessary to avoid alveolar collapse.

Moreover, the compositions of the invention also possess a very long-lasting activity. A study of the isotherms between successive compression-expansion cycles has shown a very small shift in area, which guarantees a very long activity when the compositions are used in vivo.

The artificial surfactant compositions of the invention thus meet all the criteria of an excellent exogenous surfactant and are used therapeutically in animals and humans for the treatment of disorders caused by a deficiency of endogenous pulmonary surfactant.

The following examples, which are not intended to be limiting, illustrate the invention.

EXAMPLE 1

Liposomes of artificial surfactant that is composed of a mixture of dipalmitoylphosphatidylcholine, distearoylphosphatidylcholine and soya lecithin (4M:4M:2M).

200 μmols of dipalmitoylphosphatidylcholine, 200 μmols of distearoylphosphatidylcholine and 100 μmols of soya lecithin are introduced into a round flask that has a ground neck and that has previously been washed with sterile apyrogenic distilled water and dried for 2 hours at 180° C. The mixture is dissolved in 150 ml of chloroform and the solvent is then evaporated under reduced pressure and at a temperature of from 30° to 50° C. using a rotary evaporator. The resulting fine lipid film is placed under a stream of nitrogen in order to remove all traces of residual solvent. 76.5 ml of sterile apyrogenic water are added to the flask. The whole is stirred and rotated continuously for 30 minutes. The lipids thus dispersed in the aqueous phase form liposomes spontaneously.

The liposomes are transferred to a glass cell under aseptic conditions and the lower portion of an ultrasonic probe is placed in the liposome suspension.

After 20 minutes there is obtained an opalescent solution that is virtually transparent. This solution is filtered through a filter having pores with a diameter of 0.22 μm and the filtrate is then collected and divided into "penicillin"-type bottles under sterile conditions.

The liposomes thus obtained have a concentration of artificial surfactant of 5 mg.ml$^{-1}$. They must be stored at a temperature of 4° C. and away from light.

EXAMPLE 2

Pharmaceutical composition containing 0.76 mg.ml$^{-1}$ of d,l-α-tocopherol and 20 mg.ml$^{-1}$ of artificial surfactant composed of a mixture of dipalmitoylphosphatidylcholine, distearoylphosphatidylcholine and soya lecithin (7M:1M:2M).

280 μmols of dipalmitoylphosphatidylcholine, 40 μmols of distearoylphosphatidylcholine and 80 μmols of soya lecithin and 26.5 μmols of d,l-α-tocopherol are introduced into a round flask that has a ground neck and is sterile and dry. The whole is dissolved in 100 ml of chloroform. The solvent is evaporated under reduced pressure and at a temperature of from 30° to 50° C. using a rotary evaporator, and any traces of solvent are then removed under a stream of nitrogen. 15 ml of a sterile apyrogenic solution containing sodium chloride in a concentration of 9% are added to the flask. The whole is stirred and rotated continuously for 45 minutes and the formation of liposomes is observed.

The whole is then subjected to ultrasound treatment and to sterile filtration according to the procedure described in Example 1. The sterile liposomes thus obtained have a concentration of 0.76 mg.ml$^{-1}$ of d,l-α-tocopherol and 20 mg.ml$^{-1}$ of artificial surfactant.

Innocuity Study

EXAMPLE 3

Innocuity study in rats

The innocuity of the artificial surfactant compositions of the invention was studied in rats. The trachea of animals anaesthetised with Nembutal is perforated by means of a small needle. A catheter connected to a 10 ml syringe containing the artificial surfactant is then introduced into the trachea through the perforation over a length of approximately 1 cm. The syringe is arranged on a pump and one or the other of the surfactant compositions described in Examples 1 and 2 is then perfused into the trachea in an amount of 10 mg/kg$^{-1}$ and 60 mg.kg$^{-1}$, respectively, at a rate of 0.95 ml.hour$^{-1}$. At the end of the experiment, the catheter is withdrawn, the muscular and cutaneous layers are sutured and the animal receives an intramuscular injection of 200,000 international units of Penicillin G. The animals are subsequently weighed and observed regularly until the day they are sacrificed. 48 hours or one week after the operation, the animals are sacrified by carotid section. The lungs ae removed and examined under an optical microscope and an electron microscope. No pathological indication or modification was observed.

Study of Surface Properties

EXAMPLE 4

Studies of the surface properties of the artificial surfactant compositions

The surface properties of the artificial surfactant compositions of the invention in the form of liposomes were studied with a Langmuir type film balance. Calibration in surface pressure was effected by simulating a determined surface pressure with the aid of a weight of 0.50008 g. The compositions were studied on sub-phases containing salts of physiological concentration, more precisely, 0.15 molar solutions of sodium chloride. The artificial surfactant compositions, in the form of liposomes, are spread out at the air-water interface according to the technique of Verger and Pattus (Chem. Phys. Lipids, 1976, 16, 285-291) and a latent period of 15 minutes is observed for equilibration before the start of each compression.

Figure 1:
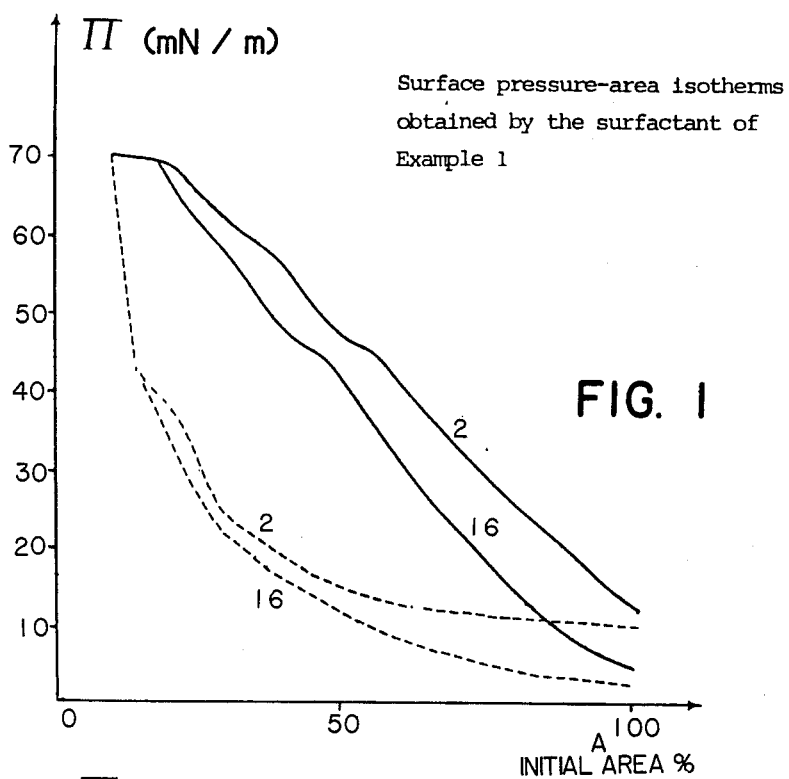
FIGS. 1 and 2 represent the isotherms of Examples 1 and 2 at 37° C. On the graphs, the continuous lines indicate compression of the films and the dotted lines indicate expansion. The numbers on the cycles indicate the serial numbers of the cycles.
Figure 2:
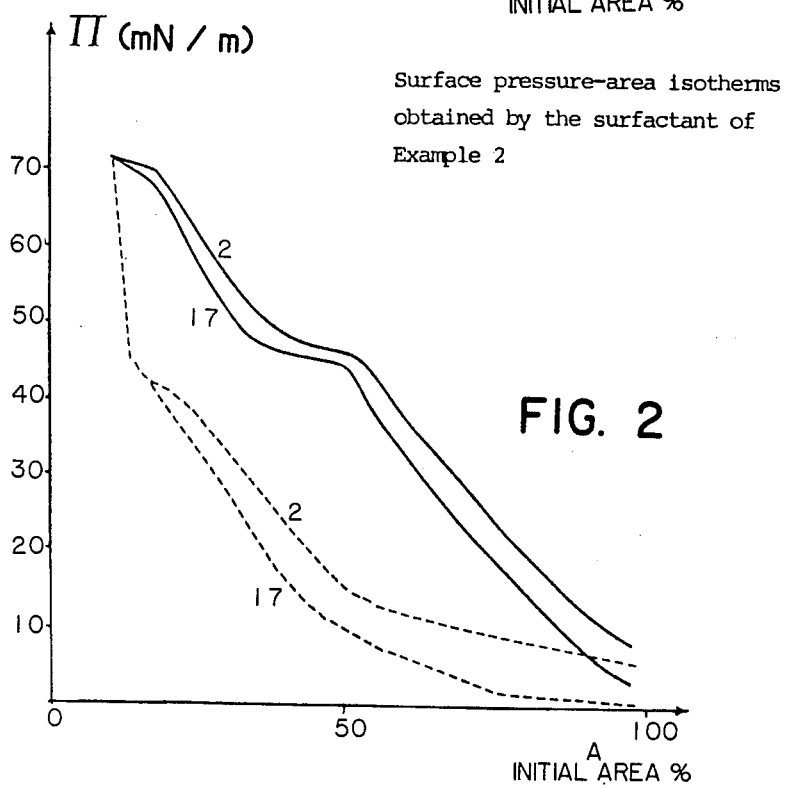

A study of these graphs leads to the following conclusions:

(1) The compositions of Examples 1 and 2 are active at 37° C.

(2) They are adsorbed spontaneously at the interface and the two collapse plateaux appear from the first cycles.

(3) The monomolecular films of the surfactant compositions of Examples 1 and 2 are able to generate a maximum surface pressure of approximately 72 mN.m$^{-1}$, a first plateau appearing at a surface pressure of approximately 46 mN.m$^{-1}$. These two plateaux, which, moreover, correspond to the coexistence of solid and liquid phases of the constituents, make it possible to obtain both a high surface pressure at the end of compression, which is necessary to avoid alveolar collapse at the biological level, and a not inconsiderable pressure on large areas which contributes to the reduction in the ventilatory effort.

(4) The surface pressure-area isotherms show that the collapse plateau remains large even after several cycles and only a slight displacement towards the smaller areas appears between the second and sixteenth (Example 1) or second and seventeenth (Example 2) compression-expansion cycles. This property is associated with the surfactant's great ability to spread out again and it shows that the loss of molecules during successive cycles, due to the passage of the collapse, is minimal. This property is very important because it guarantees the activity of the surfactant over a maximum length of time.

A study of the surface properties shows that the compositions of the invention possess all the characteristics of a good exogenous surfactant.

Clinical Study

EXAMPLE 5

Study of the immediate efficacy and clinical safety in neonates

The immediate efficacy and clinical safety of artificial surfactants were evaluated in neonates. Trials were conducted in four very premature infants with hyaline membrane disease requiring artificial ventilation and great oxygen therapy (Fi≧50%). Liposomes of artificial surfactant containing a mixture of dipalmitoylphosphatidylcholine, distearoylphosphatidylcholine and soya lecithin (4:4:2:w/w/w) (and also approximately 4M:4M:2M) were used in this study. The concentration of artificial liposome surfactant was 10 mg.ml$^{-1}$. The artificial surfactant was administered between the 4th and 12th hours of life by the direct endotracheal route. After lying the infant onto the left side, with the head turned to the right, a fine catheter was introduced into the endotracheal tube and 2 ml.kg$^{-1}$ of the product were injected directly. After reconnecting the artificial ventilation, the same procedure was repeated several minutes later with the child lying on the right side and the head turned to the left.

The clinical safety was always good. The immediate effect of the injection was evaluated by the increase in arterial oxygen ($\Delta PaO_2$) and by the possibility of decreasing the fraction of inspired oxygen ($\Delta FiO_2$). The results of these trials are reported in Table I.

TABLE I

| INFANT | GESTATIONAL AGE | WEIGHT | $\Delta PaO_2$ | $\Delta FiO_2$ |
|---|---|---|---|---|
| 1 | 29 weeks | 1,200 g | +4.5 KPa (in 5 min) | −30% (in 2 hr) |
| 2 | 29 weeks + 3 days | 1,050 g | +5.9 KPa (in 20 min) | −20% (in 3 hr) |
| 3 | 30 weeks | 1,300 g | +4.8 KPa (in 10 min) | −15% (in 1 hr) |
| 4 | 26 weeks + 4 days | 950 g | +5.4 KPa (in 10 min) | −35% (in 2 hr) |

We claim:

1. Artificial surfactant characterised in that it consists essentially of a ternary mixture of:
   (1) from 10 to 70 mol % of dipalmitoylphosphatidylcholine,
   (2) from 10 to 70 mol % of distearoylphosphatidylcholine,
   (3) from 10 to 30 mol % of soya lecithin,
   wherein the sum of the constituents indicated under 1 to 3 must, in each case, be equal to 100 mol %.

2. Pharmaceutical composition containing the artificial surfactant according to claim 1 in the form of liposomes, which, pharmaceutical composition can be used for replacing deficient endogenous pulmonary surfactant.

3. Pharmaceutical composition according to claim 2 in the form of liposomes suspended in water or in a physiologically acceptable aqueous solution.

4. Pharmaceutical composition containing one or more compounds which can be used therapeutically and which contains as carrier an artificial surfactant according to claim 1.

5. Artificial surfactant of claim 1 in the form of liposomes optionally suspended in water or in a physiologically-acceptable aqueous solution.

6. Artificial surfactant according to claim 1, characterised in that it is composed of 40 mol % of dipalmitoylphosphatidylcholine, 40 mol % of distearoylphosphatidylcholine, and 20 mol % of soya lecithin.

7. Pharmaceutical composition containing the artificial surfactant according to claim 6 in the form of liposomes, which pharmaceutical composition can be used for replacing deficient endogenous pulmonary surfactant.

8. Pharmaceutical composition according to claim 7 in the form of liposomes suspended in water or in a physiologically acceptable aqueous solution.

9. Pharmaceutical composition containing one or more compounds which can be used therapeutically and which contains as carrier an artificial surfactant according to claim 6.

10. A method for treating respiratory distress in neonates wherein endogenous pulmonary surfactant normally present is absent or deficient, comprising administering endotracheally an artificial surfactant consisting essentially of a ternary mixture of dipalmitoylphosphatidylcholine, distearoylphosphatidylcholine, and soya lecithin.

11. The method of claim 10 wherein the artificial surfactant comprises about 40 mol% of dipalmitoylphosphatidycholine, 40 mol% of distearoylphosphatidylcholine, and 20 mol% of soya lecithin and is in the form of liposomes.

12. The method of claim 10, wherein the artificial surfactant consists essentially of:
   (1) from 10 to 70 mol % of dipalmitoylphosphatidylcholine,
   (2) from 10 to 70 mol % of distearoylphosphatidylcholine,
   (3) from 10 to 30 mol % of soya lecithin, wherein the sum of the constituents indicated under 1 to 3 must, in each case, be equal to 100 mol %.

* * * * *